(12) United States Patent
Shi et al.

(10) Patent No.: US 8,271,236 B2
(45) Date of Patent: Sep. 18, 2012

(54) METHOD OF PREDICTING BREAKAGE PROPERTIES OF A PARTICULATE MATERIAL WHEN SUBJECTED TO IMPACT

(75) Inventors: Fengnian Shi, Forest Lake (AU); Toni Kojovic, Sinnamon Park (AU)

(73) Assignee: The University of Queensland, St. Lucia (AU)

( * ) Notice: Subject to any disclaimer, the term of this patent is extended or adjusted under 35 U.S.C. 154(b) by 534 days.

(21) Appl. No.: 12/373,344

(22) PCT Filed: Jul. 10, 2007

(86) PCT No.: PCT/AU2007/000953
§ 371 (c)(1),
(2), (4) Date: Sep. 18, 2009

(87) PCT Pub. No.: WO2008/006151
PCT Pub. Date: Jan. 17, 2008

(65) Prior Publication Data
US 2010/0042383 A1  Feb. 18, 2010

(30) Foreign Application Priority Data
Jul. 12, 2006 (AU) ................ 2006903745

(51) Int. Cl.
*G06F 7/60* (2006.01)
*G06F 17/10* (2006.01)
(52) U.S. Cl. .......................................... 703/2

(58) Field of Classification Search ............ 703/2
See application file for complete search history.

(56) References Cited

U.S. PATENT DOCUMENTS

| | | | |
|---|---|---|---|
| 3,401,891 A | 9/1968 | Fleeman et al. | |
| 4,860,572 A | 8/1989 | Brar et al. | |
| 2002/0077795 A1 | 6/2002 | Woods et al. | |

FOREIGN PATENT DOCUMENTS

| | | |
|---|---|---|
| JP | 2005337784 A | 12/2005 |
| WO | WO 02/40966 A2 | 5/2002 |

OTHER PUBLICATIONS

Genc et al. "Single Particle Impact Breakage Characterization of Materials by Drop Weight Testing"., Physicochemcal Problems of Mineral Processing., 2004., p. 241-255.*

(Continued)

*Primary Examiner* — Eunhee Kim
(74) *Attorney, Agent, or Firm* — Sutherland Asbill & Brennan LLP

(57) ABSTRACT

A method of predicting breakage properties of a particulate material when subjected to impact, the method including: calculating a breakage index for the particulate material using the following equation: Breakage Index=$M\{1-\exp[-f_{mat}xk-E]\}$ where: M represents the maximum breakage of particles for the particulate material; $f_{mat}$ is a material parameter that is a function of the particulate material being broken and particle size; x is the initial particle size of the particulate material prior to impact; E is a measure of the specific energy applied to the particulate material; and k is the number of impacts with specific energy E.

15 Claims, 8 Drawing Sheets is a family of t-curves

OTHER PUBLICATIONS

Shi et al., 2007, "Validation of a Model for Impact Breakage Incorporating Particle Size Effect," Int. J. Miner. Process. 82:156-163.

Morrison et al., 2007, "Modeling of Incremental Rock Breakage by Impact—For Use in DEM Model," Minerals Engineering, 20:303-309.

Sahoo, 2006, "Review: An Investigation of Single Particle Breakage Tests for Coal Handling System of the Gladstone Port," Powder Technology, 161:158-167.

Vogel et al., 2003, "Breakage Behaviour of Different Materials—Construction of a Mastercurve for the Breakage Probability," Powder Technology, 129:101-110.

Cho et al., 2003, "An Equation for the Breakage of Particles under Impact," Powder Technology, 132:161-166.

Derwent Abstract Accession No. 83-h3905k/22, Class S03 SU 945726A, (AS UKR Strength Problems) Jul. 25, 1982, Abstract.

Supplementary European Search Report for EP Application No. 07 76 3764 dated Feb. 26, 2010 (2 pages).

* cited by examiner

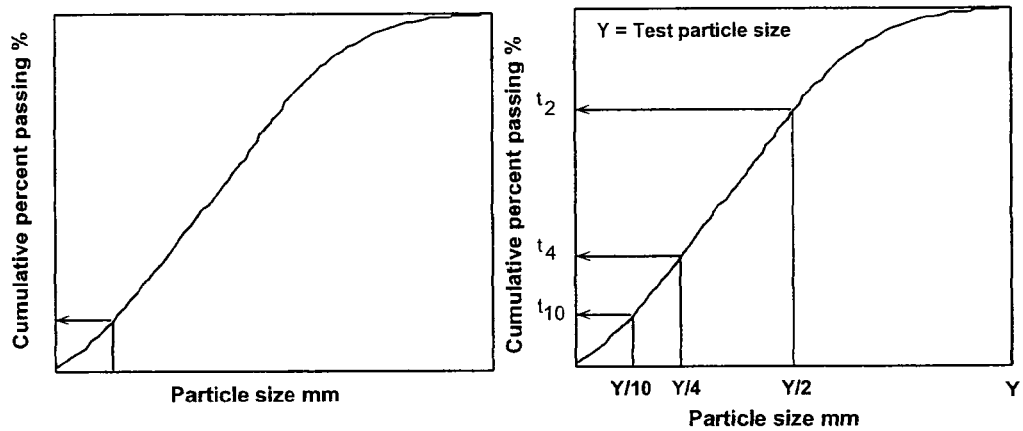
Fig 1 is a cumulative PSD
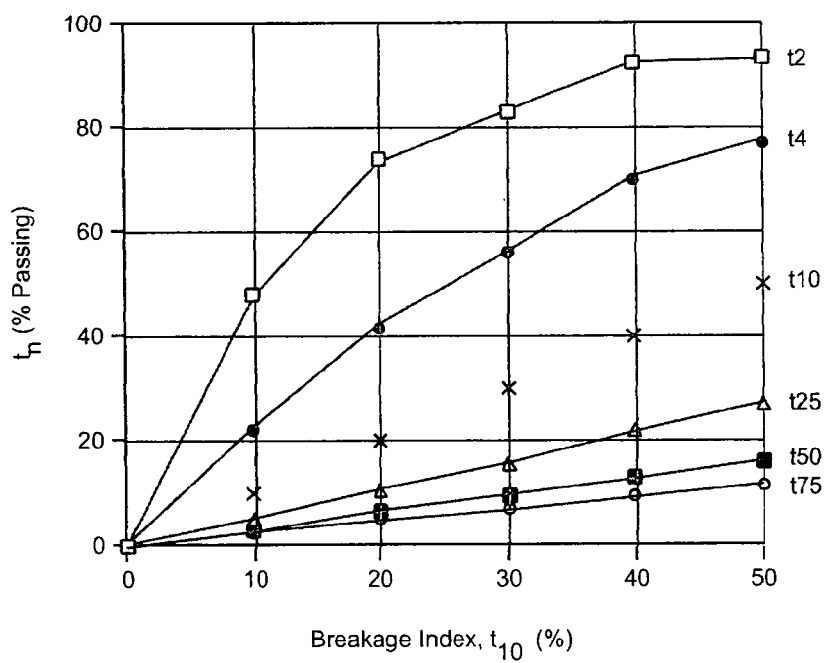
Fig 2 is a family of t-curves

| Fitted parameters | A = 59.07 | b = 0.435 | | |
|---|---|---|---|---|
| Size (mm) | Ecs (kWh/t) | Measured t10 (%) | Calculated t10 (%) | Weighted. error |
| 9.5 – 11.2 | 0.24 | 2.69 | 5.88 | 35.90 |
| | 0.42 | 5.39 | 9.85 | 34.94 |
| | 0.97 | 13.14 | 20.38 | 37.73 |
| | 1.54 | 17.39 | 28.88 | 71.52 |
| | 2.07 | 28.78 | 35.02 | 12.79 |
| | 2.63 | 35.41 | 40.23 | 6.19 |
| | 5.21 | 50.03 | 52.95 | 1.61 |
| | 10.27 | 56.14 | 58.40 | 0.86 |
| 13.2 – 16.0 | 0.22 | 3.29 | 5.49 | 13.91 |
| | 0.39 | 6.16 | 9.30 | 15.07 |
| | 1.00 | 17.69 | 20.77 | 5.05 |
| | 1.49 | 24.55 | 28.21 | 5.16 |
| | 1.99 | 32.72 | 34.27 | 0.70 |
| | 2.52 | 38.62 | 39.33 | 0.13 |
| | 5.06 | 51.29 | 52.54 | 0.28 |
| | 10.19 | 60.93 | 58.37 | 1.02 |
| 19.0 -22.4 | 0.25 | 6.24 | 6.20 | 0.00 |
| | 0.41 | 10.15 | 9.62 | 0.25 |
| | 1.02 | 22.60 | 21.12 | 0.92 |
| | 1.54 | 33.50 | 28.81 | 6.19 |
| | 2.04 | 37.28 | 34.72 | 1.66 |
| | 2.51 | 42.65 | 39.26 | 2.53 |
| | 3.78 | 52.25 | 47.65 | 3.82 |
| | 4.99 | 52.98 | 52.35 | 0.07 |
| 26.5 – 31.5 | 0.25 | 7.79 | 6.04 | 3.70 |
| | 0.41 | 11.79 | 9.60 | 3.85 |
| | 1.00 | 25.66 | 20.85 | 8.49 |
| | 1.51 | 37.28 | 28.43 | 19.84 |
| | 2.02 | 44.06 | 34.56 | 19.32 |
| | 2.52 | 48.90 | 39.31 | 17.75 |
| 37.5 – 45.0 | 0.10 | 3.80 | 2.60 | 3.56 |
| | 0.28 | 11.10 | 6.78 | 15.84 |
| | 0.40 | 13.62 | 9.41 | 12.30 |
| | 0.76 | 23.09 | 16.59 | 17.25 |
| | 1.01 | 33.66 | 21.08 | 44.40 |
| | 1.16 | 33.97 | 23.41 | 30.940 |
| 53.0 – 63.0 | 0.05 | 2.08 | 1.16 | 3.844 |
| | 0.09 | 2.63 | 2.38 | 0.21 |
| | 0.15 | 5.33 | 3.70 | 4.72 |
| | 0.20 | 10.05 | 4.89 | 24.95 |
| | 0.25 | 11.57 | 6.11 | 24.36 |
| | 0.30 | 11.62 | 7.18 | 15.98 |
| SSQ | | | | 530 |

FIG 3

| Size (mm) | A | b |
|---|---|---|
| 9.5 – 11.2 | 64.50 | 0.246 |
| 13.2 – 16.0 | 64.80 | 0.317 |
| 19.0 – 22.4 | 60.86 | 0.470 |
| 26.5 – 31.5 | 74.80 | 0.434 |
| 37.5 – 45.0 | 85.88 | 0.447 |
| 53.0 – 63.0 | 100.00 | 0.423 |

| Fitted parameters | M = 61.47 | D = x. $E_{min}$ = 3.738 | | |
|---|---|---|---|---|
| Size (mm) | Ecs (kWh/t) | Measured t10 (%) | Calculated t10 (%) | Weighted error |
| 9.5 – 11.2 | 0.24 | 2.69 | 2.46 | 0.17 |
| | 0.42 | 5.39 | 5.45 | 0.01 |
| $f_{mat}$ = 0.00786 | 0.97 | 13.14 | 13.79 | 0.31 |
| | 1.54 | 17.39 | 21.09 | 7.41 |
| | 2.07 | 28.78 | 26.80 | 1.28 |
| | 2.63 | 35.41 | 32.02 | 3.05 |
| | 5.21 | 50.03 | 47.61 | 1.11 |
| | 10.27 | 56.14 | 58.29 | 0.78 |
| 13.2 – 16.0 | 0.22 | 3.29 | 3.40 | 0.04 |
| | 0.39 | 6.16 | 6.96 | 0.98 |
| $f_{mat}$ = 0.00715 | 1.00 | 17.69 | 17.92 | 0.03 |
| | 1.49 | 24.55 | 25.29 | 0.21 |
| | 1.99 | 32.72 | 31.47 | 0.45 |
| | 2.52 | 38.62 | 36.80 | 0.80 |
| | 5.06 | 51.29 | 51.91 | 0.07 |
| | 10.19 | 60.93 | 60.05 | 0.12 |
| 19.0 -22.4 | 0.25 | 6.24 | 5.85 | 0.23 |
| | 0.41 | 10.15 | 9.88 | 0.06 |
| $f_{mat}$ = 0.00660 | 1.02 | 22.60 | 23.15 | 0.13 |
| | 1.54 | 33.50 | 31.76 | 0.85 |
| | 2.04 | 37.28 | 38.20 | 0.21 |
| | 2.51 | 42.65 | 43.02 | 0.03 |
| | 3.78 | 52.25 | 51.53 | 0.09 |
| | 4.99 | 52.98 | 55.99 | 1.61 |
| 26.5 – 31.5 | 0.25 | 7.79 | 7.43 | 0.16 |
| | 0.41 | 11.79 | 12.42 | 0.31 |
| $f_{mat}$ = 0.00584 | 1.00 | 25.66 | 27.26 | 0.94 |
| | 1.51 | 37.28 | 36.34 | 0.23 |
| | 2.02 | 44.06 | 43.07 | 0.21 |
| | 2.52 | 48.90 | 47.84 | 0.22 |
| 37.5 – 45.0 | 0.10 | 3.80 | 3.36 | 0.48 |
| | 0.28 | 11.10 | 10.27 | 0.57 |
| $f_{mat}$ = 0.00485 | 0.40 | 13.62 | 14.44 | 0.47 |
| | 0.76 | 23.09 | 25.12 | 1.70 |
| | 1.01 | 33.66 | 31.23 | 1.66 |
| | 1.16 | 33.97 | 34.24 | 0.02 |
| 53.0 – 63.0 | 0.05 | 2.08 | 1.33 | 2.53 |
| | 0.09 | 2.63 | 3.65 | 3.71 |
| $f_{mat}$ = 0.00383 | 0.15 | 5.33 | 6.08 | 0.98 |
| | 0.20 | 10.05 | 8.24 | 3.06 |
| | 0.25 | 11.57 | 10.41 | 1.11 |
| | 0.30 | 11.62 | 12.29 | 0.37 |
| SSQ | | | | 38.8 |

FIG 8

| Fitted parameters | M = 62.02 | D = x.$E_{min}$ = 4.145 | p = 0.02005 | q = -0.3851 | |
|---|---|---|---|---|---|
| Size (mm) | $E_{cs}$ (kWh/t) | Measured $t_{10}$ (%) | $E_{cs}$ (kJ/kg) | Calculated $t_{10}$ (%) | Wtd. error |
| 9.5 – 11.2 | 0.24 | 2.69 | 0.87 | 2.38 | 0.32 |
| | 0.42 | 5.39 | 1.51 | 5.52 | 0.03 |
| | 0.97 | 13.14 | 3.50 | 14.23 | 0.86 |
| | 1.54 | 17.39 | 5.55 | 21.80 | 10.55 |
| | 2.07 | 28.78 | 7.43 | 27.69 | 0.38 |
| | 2.63 | 35.41 | 9.45 | 33.05 | 1.48 |
| | 5.21 | 50.03 | 18.76 | 48.78 | 0.30 |
| | 10.27 | 56.14 | 36.97 | 59.16 | 1.53 |
| 13.2 – 16.0 | 0.22 | 3.29 | 0.81 | 3.26 | 0.00 |
| | 0.39 | 6.16 | 1.42 | 6.87 | 0.77 |
| | 1.00 | 17.69 | 3.58 | 17.98 | 0.05 |
| | 1.49 | 24.55 | 5.37 | 25.44 | 0.31 |
| | 1.99 | 32.72 | 7.18 | 31.70 | 0.30 |
| | 2.52 | 38.62 | 9.07 | 37.10 | 0.56 |
| | 5.06 | 51.29 | 18.21 | 52.37 | 0.22 |
| | 10.19 | 60.93 | 36.67 | 60.60 | 0.02 |
| 19.0 - 22.4 | 0.25 | 6.24 | 0.92 | 5.47 | 0.90 |
| | 0.41 | 10.15 | 1.47 | 9.36 | 0.57 |
| | 1.02 | 22.60 | 3.66 | 22.30 | 0.04 |
| | 1.54 | 33.50 | 5.53 | 30.82 | 2.02 |
| | 2.04 | 37.28 | 7.33 | 37.27 | 0.00 |
| | 2.51 | 42.65 | 9.04 | 42.16 | 0.05 |
| | 3.78 | 52.25 | 13.59 | 50.97 | 0.29 |
| | 4.99 | 52.98 | 17.98 | 55.74 | 1.36 |
| 26.5 – 31.5 | 0.25 | 7.79 | 0.89 | 6.95 | 0.86 |
| | 0.41 | 11.79 | 1.47 | 11.75 | 0.00 |
| | 1.00 | 25.66 | 3.60 | 26.19 | 0.10 |
| | 1.51 | 37.28 | 5.43 | 35.21 | 1.09 |
| | 2.02 | 44.06 | 7.28 | 42.02 | 0.89 |
| | 2.52 | 48.90 | 9.06 | 46.94 | 0.74 |
| 37.5 – 45.0 | 0.10 | 3.80 | 0.37 | 3.24 | 0.79 |
| | 0.28 | 11.10 | 1.01 | 10.16 | 0.75 |
| | 0.40 | 13.62 | 1.43 | 14.33 | 0.35 |
| | 0.76 | 23.09 | 2.73 | 25.05 | 1.58 |
| | 1.01 | 33.66 | 3.65 | 31.20 | 1.70 |
| | 1.16 | 33.97 | 4.18 | 34.23 | 0.02 |
| 53.0 – 63.0 | 0.05 | 2.08 | 0.16 | 1.37 | 2.28 |
| | 0.09 | 2.63 | 0.34 | 3.93 | 6.04 |
| | 0.15 | 5.33 | 0.53 | 6.60 | 2.85 |
| | 0.20 | 10.05 | 0.72 | 8.98 | 1.08 |
| | 0.25 | 11.57 | 0.90 | 11.34 | 0.04 |
| | 0.30 | 11.62 | 1.07 | 13.39 | 2.54 |
| SSQ | | | | | 46.6 |

FIG 11

| Fitted parameters | M = 63.77 | D = x.$E_{min}$ = 4.442 | p = 0.0146 | q = -0.3126 | |
|---|---|---|---|---|---|
| Size (mm) | $E_{cs}$ (kWh/t) | Measured $t_{10}$ (%) | $E_{cs}$ (kJ/kg) | Calculated $t_{10}$ (%) | Wtd. error |
| 13.2 – 16.0 | 1.00 | 17.69 | 3.58 | 17.78 | 0.004 |
| | 10.19 | 60.93 | 36.67 | 60.60 | 0.06 |
| 26.5 – 31.5 | 0.25 | 7.79 | 0.89 | 7.75 | 0.002 |
| | 1.00 | 25.66 | 3.60 | 26.23 | 0.12 |
| | 2.52 | 48.90 | 9.06 | 47.01 | 0.69 |
| 37.5 – 45.0 | 0.28 | 11.10 | 1.01 | 10.16 | 0.03 |
| | 1.16 | 33.97 | 4.18 | 34.23 | 0.13 |
| SSQ | | | | | 1.04 |

FIG 12

| | A | b | Axb |
|---|---|---|---|
| 42 experiments | 59.07 | 0.435 | 25.70 |
| The invention | 56.81 | 0.475 | 26.98 |

METHOD OF PREDICTING BREAKAGE PROPERTIES OF A PARTICULATE MATERIAL WHEN SUBJECTED TO IMPACT

CROSS REFERENCE TO RELATED APPLICATIONS

This application claims the priority benefit of PCT/AU2007/000953 filed on Jul. 10, 2007 and Australian Application No. 2006903745 filed Jul. 12, 2006.

FIELD OF THE INVENTION

This invention relates to a method of predicting breakage properties of a particulate material when subjected to impact.

This invention relates particularly to a method of predicting the size distribution of broken particles when a feed ore containing mineral to be recovered is subjected to impact of the type that occurs in comminution operations. Particulate ore material undergoes comminution to reduce the size of the particles and to reduce the spread of sizes of particles prior to the recovery of the valuable mineral in the downstream mineral processing operations which typically may include hydrometallurgical or pyrometallurgical operations. It will therefore be convenient to hereinafter describe the invention with reference to this example application. However it is to be clearly understood that the invention has broader application.

BACKGROUND TO THE INVENTION

Comminution or breakage of particles in apparatus such as mills and crushers is an important mineral processing operation. These operations receive run of mine ore from the mine and then reduce the size of the particles before the ore is subjected to further processing to liberate the mineral values within the ore. The capital cost of installed mills and crushers is extremely high. Further the energy demand of mills and crushers is also very high and the efficiency of converting input energy into breakage of particles is extremely low. Consequently there is an ongoing need to develop an improved understanding of these processes so as to enable engineers to operate these processes more efficiently.

The modeling of mineral processing operations is a tool that is widely used throughout the mineral processing operations for this purpose. These models assist in understanding the process and can be used in process development, optimizing plant performance and also in the design of new plants. In particular the model can be used by engineers to help understand the breakage of particles in a mill for example. This understanding in turn can lead engineers to adjust mill settings and this can result in more effective operation in the mill.

The model can also be used for the simulation of plant performance. The simulation of comminution apparatus such as autogenous (AG) and semi-autogenous (SAG) mills, ball mills and crushers is used widely by the mining industry for the design and optimization of plants and also general trouble shooting. However it will be readily appreciated that the value of any simulation model will depend on the underlying accuracy and validity of the models used to define particle breakage in the mill or crusher. Applicant provides simulation services in relation to various comminution apparatus and is aware of limitations in many of the breakage functions used in its simulations. Applicant therefore recognizes the benefits to be obtained from any improvement in the modeling of particle breakage due to impacts of the type that occur in comminution apparatus.

In the modeling of a comminution process the likely size distribution of the progeny particles produced as a result of an impact needs to be determined. Further the effect of feed particle size on the size distribution of the product particles and the influence of the energy applied to the particle by the impact needs to be understood.

The first step in this process is to obtain experimental data on the distribution of product particles as a function of certain impact energies and feed particle size. This is done by conducting particle breakage tests of the type known in the prior art as the pendulum test and the drop test.

These tests involve subjecting a certain size of particle to an impact at a specific energy and then measuring a breakage index that can be converted into the size distribution of the resultant particles. These tests produce a product particle size distribution for the breakage of individual particles as a function of their size and also the amount of applied specific energy that produces the breakage.

A particle size distribution (PSD) can be represented by means of a graph showing the relative amounts of the various sizes on the y axis plotted against the different particle sizes on the x axis. The particle size distribution of a population of broken or product particles produced as a result of a collision or impact can be represented by means of a particle size distribution graph, e.g. a cumulative size distribution that plots the cumulative percentage by weight of broken particles in a population underneath a certain size against that particle size. The percentage by weight of particles below a given size is determined by classification. FIG. 1 shows a graph of the cumulative size distribution of broken particles produced by an impact.

While it is possible to describe the size distribution of broken particles as a result of a collision by a PSD curve such as that shown in FIG. 1 other ways of representing this information have evolved in this art.

One such technique is to represent this information by means of a breakage index called the $t_{10}$ index or product fineness index. In essence the $t_{10}$ index provides all the information necessary to obtain the full PSD. The $t_{10}$ index can be converted into a full PSD curve by means of a graph known as the family of t-curves which was first published by Narayanan. FIG. 2 shows a graph of the family of t-curves. The form of the t-curves and the manner in which they are derived will be discussed below.

The drop weight tests cause an impact of specific energy to be applied to a particle and the broken particles resulting from the impact are collected and then classified. The broken particles are classified using a standard set of sieves of different sizes. The discrete weight percentages passing through each sieve are then converted to cumulative weight percent of the feed particles passing through the screen.

The weight of particles passing through screens having the sizes of $1/50^{th}$, $1/25^{th}$, $1/10^{th}$, $1/4$ and $1/2$ of the initial screen size is then calculated from the cumulative PSD by a cubic spline calculation that is known in the art. The cumulative weight percentage passing through the $1/75^{th}$ screen is called the $t_{75}$ index, the amount passing the $1/50^{th}$ screen is called the $t_{50}$ index, the amount passing the $1/10$th screen is called the $t_{10}$ index and so on. By repeating the process across different energy levels a set of $t_n$ indices can be built up that provide the data that enable the family of t-curves to be obtained.

In FIG. 2 the $t_{75}$, $t_{50}$, $t_{25}$, $t_{10}$ etc indices are plotted on the y axis against the $t_{10}$ index on the x axis. Several independent researchers in the field including Narayanan have confirmed that the mathematical relationships defined by the t-curves does in fact accurately represent the breakage of particles at different energy levels and that this family of curves is basically universal for rock materials.

Thus in the absence of specific data on the family of t-curves for a given material a default set of curves may be used that applies to most materials such as rock. However if the breakage characteristics of the material being used are quite different from the breakage of rock then actual breakage tests results for that particular material may be used to generate a family of t-curves. However for most mineral ores this will not be necessary and the default set of t-curves may be used. Yet further some of the published information on t-curves for certain materials is presented in the form of reference tables.

The t-curves are very useful because once the $t_{10}$ is determined for a material, e.g. as a result of drop test, then the t-curves can be used to transform or convert the $t_{10}$ value into a full cumulative particle size distribution as shown in FIG. 1. Put another way the $t_{10}$ index is a convenient form of shorthand for representing the particle size distribution that can be obtained from the t-curves or reference tables that are available in the literature, or from t-curves derived from actual breakage tests for that material.

The PSD is obtained from the family of t-curves by extending a vertical line up from the measured $t_{10}$ index on the x axis and intersecting the $t_n$ curves to obtain plot points for $t_2$, $t_4$, $t_{25}$, $t_{50}$ and $t_{75}$. These points are then used to plot out the cumulative PSD.

As described above the $t_{10}$ index is the weight percentage of the population of broken particles that pass through a screen having openings that are 1/10th of the initial mean size of the particle subjected to the impact. It is a measure of the fineness of the population of particles produced by an impact. The higher the value of $t_{10}$ the greater is the weight of fines in the product population.

Applicant has over time used the $t_{10}$ index as a measure or finger print of the particle size distribution of the broken particle population. It is a convenient tool because once the $t_{10}$ index is established then the full cumulative PSD can be obtained from the t-curves. While the specific choice of $t_{10}$ to define product fineness is arbitrary in some respects, it has become widely used in the field and this is why it is given weight in this specification.

As indicated briefly above, drop weight tests are used to calculate the product fineness index $t_{10}$ for the particles that are subjected to the impact tests.

Once the $t_{10}$ has been calculated for the test particles then the test data is fitted to a model to calculate the material specific parameters for that ore. Once these parameters have been determined they are plugged into the model. The model can only be used to predict the size distribution of broken particles after these parameters have been calculated.

A model that has been used in the prior art to predict the distribution of broken particles as a result of a particle undergoing an impact is the following equation (hereinafter referred to as the prior art JK model).

$$t_{10}=A(1-e^{-b \cdot E_{cs}}) \quad (1)$$

where:
$t_{10}$ index is the percent by weight of the initial mass of particles passing through a screen having mesh openings that are 1/10$^{th}$ of the initial mean size of the test particles;
$E_{cs}$ is the specific comminution energy that is applied to the impact expressed in kWh/t;
A and b are impact breakage parameters that depend on the material, e.g. ore that is being broken and these are therefore different for different ores and take into account the different breakage behavior of the different ores.

This model was developed by the Julius Kruttschnitt Mineral Research Centre (JKMRC) and has been used widely for over twenty years. The equation above for the $t_{10}$ product fineness is an exponential function. The parameter A is the level at which $t_{10}$ reaches an asymptote that represents the maximum extent of particle breakage that can be obtained. Additional impact energy above this level does not produce increased levels of particle breakage.

By contrast A*b is the slope of the curve at its initial take away point towards the lower end of the curve. The product of A and b is used for comparison between different materials.

The breakage properties of a particular ore are conveniently characterized and expressed by the product of A*b. Many mining companies have developed extensive databases of A and b parameters and also A*b results for many different ore bodies. The database of A and b values are generally developed over a long period of time and can be used repeatedly by the company. The A*b value is characteristic of the particular rock that has been tested. As long as the rock material remains the same, the values of A and b do not need to be re-determined each time the particle breakage of the material is studied.

As indicated briefly above the physical breakage test results produced by the drop weight apparatus are used to calculate characteristic A and b parameters for each ore that is tested. Standard numerical methods such as statistical curve fitting techniques are used to calculate A and b for each particulate material from the drop weight test results. The curve fitting techniques start with estimated values for A and b and then a new $t_{10}$ is calculated with these parameters. The calculated value of $t_{10}$ is then compared with the experimentally determined value of $t_{10}$ from the drop weight tests to calculate the error. This error is then divided by the standard deviation and then squared. This process of calculating a new $t_{10}$ with the estimated parameters A and b is then repeated for all different particle sizes and each energy level of each particle size. This produces a squared error for each of the test results. The squared errors are then summed to yield a sum of the squared errors. Based on this result new estimates are selected for A and b and another iteration of the same sequence of calculations is carried out to calculate a new set of $t_{10}$ values. This produces another sum of the squared errors that can be compared with the previous sums of the squared errors. These iterations are repeated until a minimum sum of the squared errors is obtained which fixes the values of A and b.

The values of parameters A and b that produce the minimum sum of the squared errors represent the best fit of the model to the experimental data and these are the A and b values calculated for that material.

One limitation of using the prior art JK model defined in Equation 1 is that the model calculates one value for parameter A and one value for parameter b for a given particle sample which has a range of particle sizes. The assumption implicit in this model therefore is that the breakage parameters are not affected by particle size. Put another way it assumes that particles of different sizes would be broken in the same way when subjected to the same impact energy. Thus the model effectively calculates an average set of A and b parameters for all particle sizes.

Applicant has shown some test work with a Mt Coot-tha quarry material having average particle sizes covering at least the range of 10.3 mm to 57.8 mm.

The particles of the quarry material were subjected to testing with a drop weight tester to determine the $t_{10}$ index for six different particle sizes using a number of different energies for each particle size. FIG. 3 shows the drop weight test results for the Mt Coot-tha material as well as the curve fitting calculations used to fit the JK model to the data to obtain values for the parameters A and b. In addition the calculations that were carried out to calculate A and b by the numerical curve fitting techniques described above are also shown in FIG. 3. This results in a value for the parameter A of 59.07 and parameter b of 0.435 for this Mt Coot-tha quarry material.

The JK prior art model was then plotted on a graph as a single curve of $t_{10}$ against specific breakage energy ($E_{cs}$) and this graph is shown in FIG. 4 of the drawings. The individual points obtained from the drop weight test data were also plotted on this curve. This graph therefore shows how closely the model fits the test results. It is clear from the graph in FIG. 4 that the single curve representing the model reflects an average curve for the test results across the different test particle sizes. There are data points above the model line and data points below the line.

Applicant recognized the limitations of the prior art JK model illustrated by the graph in FIG. 4 and started to investigate the influence of particle size on particle breakage.

In order to demonstrate the influence of particle size on particle breakage Applicant calculated the model parameters A and b separately for each of the different sizes of particles of the Mt Coot-tha material in FIG. 3. The different values for A and b determined for each particle size are shown in the table of FIG. 5. The differences in the values of A and b calculated for the different particle sizes were significant for some particle sizes.

Each of the parameters A and b was then used to plot individual curves for each of the particle sizes using the JK model defined in Equation 1. FIG. 6 shows a family of curves with each curve representing the JK prior art model applied to a different particle size. In essence this family of curves shows that different sizes of particles have different A and b values and that the material breakage parameters are in fact a function of the size of the particle as well as the material that is being broken.

As a general proposition the JK model curves of the larger particles sit higher than the curves for the smaller particles. This tends to indicate that larger particles are easier to break than smaller particles. This accords with the Applicant's experimental work and Applicant believes that this can be explained by the fact that the crack density of larger particles is much greater than that of smaller particles.

Further each of the individual curves calculated for one particle size represents a close and consistent fit with the test data showing that it fitted the data better than the FIG. 4 graph. This shows that the underlying assumption in the prior art JK model that different sized particles break in the same way is not accurate.

In a particle breakage apparatus such as an AG/SAG mill the feed stream of particulate material typically contains a wide range of particle sizes. For example the feed stream may comprise particles having a size range from 200 mm down to smaller than 1 mm. In a crusher the range of feed particle sizes can be even greater than this. Clearly therefore it would be advantageous if a method of characterizing the breakage of an ore could be devised that took into account the effect of size on the breakage of the particles. This would lead to an improved method of characterising ore breakage. This in turn would have the potential to lead to improved modeling of particle breakage in comminution apparatus, in particular discrete element modeling.

Applicant has looked at ways of developing the JK model to account for the effect of particle size. If the effect of particle size could be worked into the model it would have the potential to produce an improved fit with the test results.

Applicant initially looked at adapting the prior art JK model to account for different particle sizes. For example, Applicant experimented with ways of incorporating the effects of particle size into the parameters A and b used in the prior art model Equation 1. Specifically, Applicant investigated whether there is a relationship between initial particle size and the product of A and b calculated for the different sizes of particles.

In FIG. 7 A*b has been plotted against the initial mean particle size for each particle size. As is clearly shown in the graph no consistent relationship between the fitted values of A and b for each size and initial particle size could be established. The shape of the graph was quite different for different particles. Further the individual plots of A*b versus size did not indicate any relationship between A*b and particle size that could be described by a mathematical formula.

It would have been useful if such a relationship had existed between A*b and particle size as the prior art JK model could have then been adapted by defining the relationship between A*b and particle size and inserting the relationship into the prior art model equation. However, no mathematical relationship between the parameters A and b and particle size could be defined.

Accordingly, there is a need to develop a new model for determining breakage properties, and more particularly the likely distribution of broken particles, when a feed particle of a certain material, for example an ore, is subjected to an impact with a certain amount of energy wherein the model takes into account the effect of the size of the feed particle.

SUMMARY OF THE INVENTION

According to one aspect of this invention there is provided a method of predicting breakage properties of a particulate material when subjected to impact, the method including:

calculating a breakage index for the particulate material using the following equation:

$$\text{Breakage Index} = M\{1 - \exp[-f_{mat} \cdot x \cdot k \cdot E]\} \quad (2)$$

where:

M represents the maximum breakage of particles for the particulate material;

$f_{mat}$ is a material parameter that is a function of the particulate material being broken and particle size;

x is the initial particle size of the particulate material prior to impact;

E is a measure of the specific energy applied to the particulate material; and k is the number of impacts with specific energy E.

The parameter M is specific to the particulate material and the parameter $f_{mat}$ is a function of the material and particle size which may be calculated separately for each particle size as discussed below in more detail.

Advantageously, the method can be used to predict the size distribution of broken progeny particles from a certain sized particle of the particulate material. The model specifically takes into account the effect of feed particle size on particle breakage. Firstly x which is particle size is a variable in the equation. Secondly particle size is also accounted for in the parameter $f_{mat}$. In the model the size distribution of broken particles is more particularly a function of the energy applied to the particle, the size of the particle and the number of impacts undergone by the particle.

The measure of specific energy (E) that is applied to the particle may be calculated by the equation:

$$E = E_{cs} - E_{min} \quad (3)$$

where:

$E_{cs}$ is the mass specific breakage energy and may be expressed in J/kg or kWh/t; and $E_{min}$ is the threshold energy below which breakage does not occur for particle size x, and again this may be expressed in J/kg or kWh/t.

M may be expressed as a percentage and x may be measured in units of m. The material property $f_{mat}$ may be measured in units of kg/J.m if $E_{cs}$ and $E_{min}$ are expressed in J/kg.

The threshold energy may be calculated by the equation:

$$E_{min} = D/x \quad (3')$$

where:

D is a material specific constant and may be expressed in J/kg.m or kWh/t.m; and x is the average particle size in m.

The breakage index may comprise a measure of the weight of broken particles below a certain size expressed as an amount relative to the weight of the original feed particles.

In particular the breakage index may be the weight of broken particles expressed as a percentage of the weight of the original feed particles that pass through a screen of a certain size.

Conveniently, the breakage index is the weight percentage of the broken particles passing through a screen having openings that are $1/10^{th}$ of the mean size of the feed particles. That is, the $t_{10}$ index.

The method preferably includes the further step of converting the breakage index into a particle size distribution, for example a cumulative particle size distribution.

The breakage index, for example the $t_{10}$ index, may be converted to a particle size distribution by plotting the particle size distribution (PSD) off a one parameter family of t-curves that plots $t_n$ against $t_{10}$. A default set of t-curves may be used to plot the PSD for most rock materials. However, if the material breakage properties differ greatly from rock then the t-curves can be fitted to a model using experimental data in the usual way.

The parameters M and $f_{mat}$ may be provided for use in the equation. That is they may have been previously determined from test data.

Alternatively the method may include determining values for the parameters M and $f_{mat}$ for the material that is being modeled and the different particle sizes.

The values for the parameters M and $f_{mat}$ may be determined by obtaining test results on the breakage of particles of particular sizes and then calculating values for M and $f_{mat}$ using statistical curve fitting techniques.

$E_{min}$ can be provided or can be determined along with M and $f_{mat}$. Alternatively, $E_{min}$ may be experimentally determined.

The physical test results on the breakage of different sizes of particles, if required, may be obtained by means of a drop weight tester, a pendulum tester or other apparatus.

The variable k, which represents the number of impacts to which the particle is subjected at energy E, can be used to account for a situation where a particle undergoes a number of impacts and the breakage is due to the cumulative effect of these impacts. For example, in a mill the particles can be subjected to several smaller incremental impacts rather than one large impact as the mill rotates.

The variable k therefore takes this into account and the model predicts the particle size distribution as a net result of all the impacts.

Thus, if a particle undergoes several smaller impacts instead on one large impact the effect of this multiple of impacts is taken into account by k. For example, in a ball mill a particle may undergo several incremental impacts as the mill rotates. This results in breakage that is different than is apparent if the particle undergoes a single large impact.

According to another aspect of this invention there is provided a method of determining a material breakage parameter ($f_{mat}$) for a material as a function of the size of a particle, the method including:

calculating the material breakage parameter according to the following equation:

$$\text{material breakage parameter } f_{mat.} = p \times x^{-q} \quad (4)$$

where:

x is the initial particle size prior to breakage; and p and q are material parameters that take into account the effect that particle size has on impact breakage.

The material breakage parameter $f_{mat}$ is a function of the material being broken and particle size and can be expressed as a power equation. The material breakage parameter decays with increasing particle size. The rate of decay of the power equation may be different for different materials and this is reflected in the equation by different p and q values.

The parameters p and q may be provided. Alternatively, the method may include determining p and q by fitting test data to the equation above.

The initial particle size x may be expressed in m.

Applicant has recognized the advantages that could be obtained by identifying a consistent functional relationship between the material parameter $f_{mat}$ and the size of a particle. The material parameter $f_{mat}$ can be determined from particle breakage data and when it is plotted against particle size it has a shape that is consistent for all materials. Further, Applicant has been able to describe the functional relationship between $f_{mat}$ and particle size by means of the mathematical equation above.

The mathematical equation describes the relationship with particle size very closely. As a result fewer test results need to be obtained to fit the model to the test results.

The mathematical Equation 4, used to define the relationship between $f_{mat}$ and particle size above, can be substituted into the Equation 2, defined in the first aspect of the invention, to streamline this equation.

As such, according to yet another aspect of this invention there is provided a method of predicting breakage properties of a particulate material when subjected to impact, the method including:

calculating a breakage index for the particulate material using the following equation:

$$\text{Breakage Index} = M\{1 - \exp[-p \cdot x^{(1-q)} \cdot k \cdot E]\} \quad (5)$$

where:

M represents the maximum breakage of particles for the particulate material;

E is a measure of the specific energy applied to the particulate material;

k is the number of impacts with specific energy E;

x is the initial particle size of the particulate material prior to impact;

p and q are material parameters for a particular material that take into account the effect that particle size has on impact breakage.

As described above, the measure of specific energy (E) that is applied to the particle may be calculated by the equation:

$$E = E_{cs} - E_{min} \quad (3)$$

Once again, $E_{cs}$ is the mass specific breakage energy and may be expressed in J/kg or kWh/t. $E_{min}$ is the threshold energy below which breakage does not occur and again this may be expressed in J/kg or kWh/t.

M may be expressed as a percentage, and the particle size x may be expressed in m.

As with the earlier aspect of the invention, the breakage index may comprise a measure of the weight of broken particles below a certain size expressed as an amount relative to the weight of the original feed particles. In particular the breakage index may be the weight of broken particles expressed as a percentage or fraction of the weight of the original feed particles that pass through a screen of a certain size. Conveniently, the breakage index is the weight percentage of the broken particles passing through a screen having openings that are $\frac{1}{10}^{th}$ of the mean size of the feed particles. That is, the $t_{10}$ index.

Once again, the method preferably includes the further step of converting the breakage index into a particle size distribution, for example a cumulative particle size distribution. The breakage index, for example the $t_{10}$ index, may be converted to a particle size distribution by plotting the PSD off a one parameter family of t-curves that plots $t_n$ against $t_{10}$.

The parameters M, p and q may be provided for use in the equation. That is they may have been previously determined from test data and be provided for use in the model.

Instead, the method may include determining values for the parameters M, p and q for the material that is being modeled. The values for the parameters M, p and q may be determined by providing test results on the breakage of particles of particular sizes and then calculating values for M, p and q using statistical curve fitting techniques. The physical test results on the breakage of different sizes of particles may be obtained by means of a drop weight tester, a pendulum tester or other apparatus.

$E_{min}$ can be provided or it can be determined by curve fitting techniques. Alternatively $E_{min}$ may be experimentally determined.

The variable k, which represents the number of impacts to which the particle is subjected at energy E, can be used to account for a situation where a particle undergoes a number of impacts as was the case in the first aspect of the invention.

This model for predicting breakage properties, and more particularly for predicting particle size distribution, as a result of at least one collision can be used in the modelling of all particle breakage unit operations including milling, crushing and grinding. The model of particle breakage is only one step in the simulation of a mill or a crusher operation. However, as this is perhaps the most important factor in the operation of the mill or crusher, it is important that the model predicts the breakage properties, and more particularly particle size distribution, accurately.

According to yet another aspect of this invention there is provided a method of predicting breakage properties of a particulate material when subjected to impact, the method including:

calculating a $t_{10}$ index for the particulate material using the following equation:

$$t_{10}=M\{1-\exp[-p \cdot x^{(1-q)} \cdot k(E_{cs}-E_{min})]\} \tag{6}$$

where:
M represents the maximum breakage of particles for the particulate material;
$E_{cs}$ is the mass specific breakage energy of the impact;
$E_{min}$ is the threshold energy below which breakage does not occur;
k is the number of impacts with specific energy ($E_{cs}-E_{min}$);

x is the initial particle size prior to impact; and
p and q are material parameters that take into account the effect that particle size has on impact breakage.

For repeat impacts of different magnitude the applied specific energy ($E_{cs}-E_{min}$) of the discrete impacts can be summed up from the first impact to the kth impact. This then models the breakage index produced by the sum of all these impacts.

The particle size x may be expressed in m. The parameters $E_{cs}$ and $E_{min}$ may be expressed in J/kg or kWh/t.

The values of the parameters M, p and q may be provided for use in the equation or may be calculated by curve fitting techniques from particle breakage test data.

The method may include the further step of transforming the $t_{10}$ index into a predicted particle size distribution of product particles, e.g. in the manner described above for the preceding aspects of the invention.

It will be appreciated from the above description that mathematically, Equation 6 is derived from Equation 6' below by combining the term x.

$$t_{10}=M\{1-\exp[-p \cdot x^{-q} \cdot k \cdot x(E_{cs}-E_{min})]\} \tag{Eq. 6'}$$

In determining the model parameters, $D=x \cdot E_{min}$ is set and D is fitted to the experimental data. The variable $E_{min}$ is back calculated from D by Equation 3' for various particle sizes. This assumption is based on the rock fracture theory that $x \cdot E_{min}$ is a constant for a material, and is size independent. Thus the back calculated $E_{min}$ is size dependant—the smaller particle having larger $E_{min}$, indicating that the smaller particle requires larger minimum energy to cause fracture. This agrees with many observations that within the contact area during an impact the smaller particles have less initial flaws or cracks, leading to higher fracture energy required (i.e. larger $E_{min}$).

The advantage of using this method to determine $E_{min}$ is that it is only necessary to fit one parameter D, rather than fitting the $E_{min}$ for individual sizes. It will be appreciated that the latter would require more tests on different particle sizes in order to fit various $E_{min}$ with statistically valid results, and such fitted $E_{min}$ may not be size-consistent.

The method may include any one or more of the optional features described above in the preceding aspects of the invention.

DETAILED DESCRIPTION OF THE INVENTION

A method in accordance with this invention may manifest itself in a variety of forms. It will be convenient to hereinafter provide a detailed description of the invention with reference to some examples. The purpose of providing this detailed description is to instruct persons having an interest in the subject matter of the invention how to put the invention into practice. It is to be clearly understood however that the specific nature of this detailed description does not supersede the generality of the preceding statements. In the drawings:

FIG. 1 is a graph showing a cumulative particle size distribution of product particles produced by an impact;

FIG. 2 is a family of t curves plotting $t_n$ curves against the $t_{10}$ index;

FIG. 3 is a table showing a set of drop weight data for Mt Coot-tha quarry material that is subjected to particle breakage and also showing how the test data is fitted to the prior art JK model of particle breakage;

FIG. 8 is a table showing the drop weight data of FIG. 3 fitted to the new JK model of particle breakage forming the invention using statistical curve fitting techniques to produce values for M, D ($=x \cdot E_{min}$) and $f_{mat}$;

FIG. 11 is a table showing the drop weight data used in FIG. 3 fitted to the new model of particle breakage to produce values for p, q and D ($=x \cdot E_{min}$);

FIG. 12 is a table showing how the parameters that were fitted in 42 tests in FIG. 11 can be fitted with just 7 tests of particle breakage; and FIG. 13 is a table showing a comparison of the ore hardness indicator A*b determined using 42 particle breakage tests compared with that predicted by the invention using 7 drop weight tests.

COMPARATIVE EXPERIMENTAL WORK COMPARING NEW MODEL DEFINED IN THIS APPLICATION WITH THE PRIOR ART METHOD

The Applicant has conducted some comparative modeling utilizing data obtained from drop weight tests. The data relates to a particulate material that is Mt Coot-tha Hornfel quarry material.

The drop weight test data is shown in FIG. 3. Basically it comprises six different particle sizes and about eight different specific energies for each particle size. This produced a total of 42 test results.

The data was fitted to the prior art JK model according to well known statistical curve fitting techniques. This produced values for the parameters A and b for the prior art JK model. The statistical curve fitting techniques have been described in some detail in the background to the invention. The table in FIG. 3 shows generally the manner in which the data is processed to obtain values for A and b of 59.07 and 0.435. First initial values for A and b are estimated. New values for $t_{10}$ are then calculated using the prior art model shown in Equation 1. The weighted error of calculated $t_{10}$ and actual $t_{10}$ determined from the drop weight tests is obtained by subtracting the one from the other and this error is then divided by the standard deviation. This result is then squared. The same calculations are repeated for all the particle sizes and all the specific energy levels for these particle sizes. The results are added up to produce the sum of the squared errors. Further iterations are then done until a minimum sum of squared errors is obtained. This represents the best fit for the values of A and b and these are the values that are then used in the model.

Figures 4, 5:
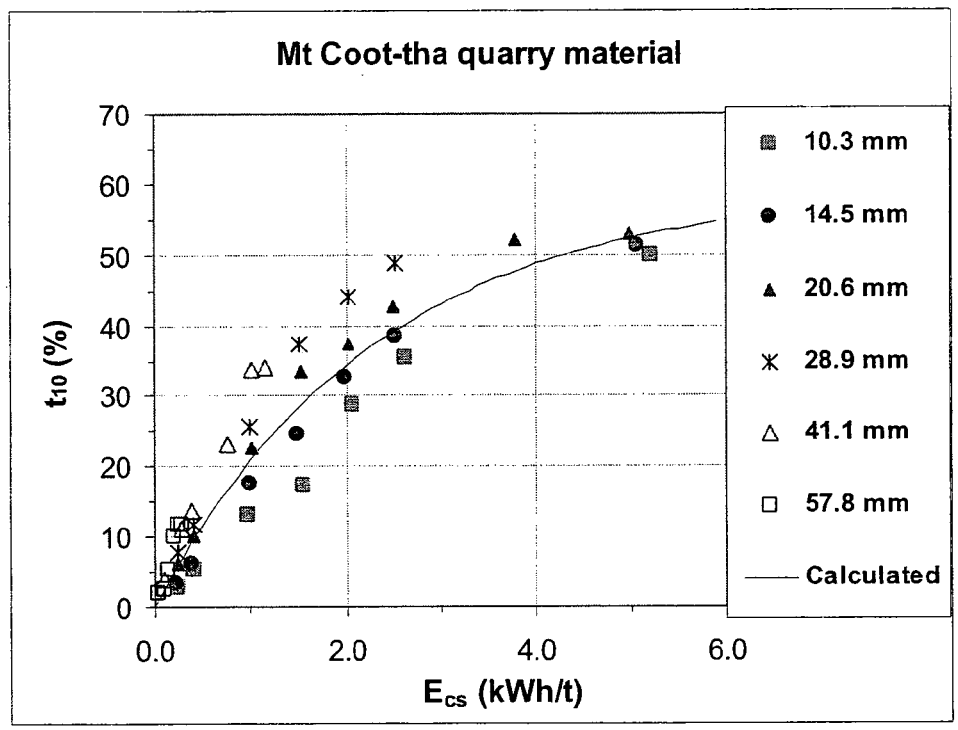
FIG. 4 is a graph showing the JK prior art breakage model fitted to the set of particle breakage data for Mt Coot-tha quarry material shown in FIG. 3.
FIG. 5 is a table showing the parameters A and b calculated for each of the particle sizes using the test breakage data shown in FIG. 3.

The prior art JK model is shown as a graph in FIG. 4 where $t_{10}$ (%) is plotted as a co-ordinate on the y axis against specific input energy $E_{cs}$ (kWh/t) on the x axis. The model defines an exponential curve that has an asymptote or limiting value of A.

In addition the individual plots of the points of the drop weight tests are also plotted on the graph of FIG. 4. It will readily be observed that the model does not fit the results closely and many of the tests points are spaced some distance away from the line. In essence the line has about half of the individual test points above the line and about half the individual test points below the line.

The curve fitting calculations produce a single value of A and b for all test results across all particle sizes. Thus the model appears to represent an average A and b for the different particle sizes.

Figure 6:
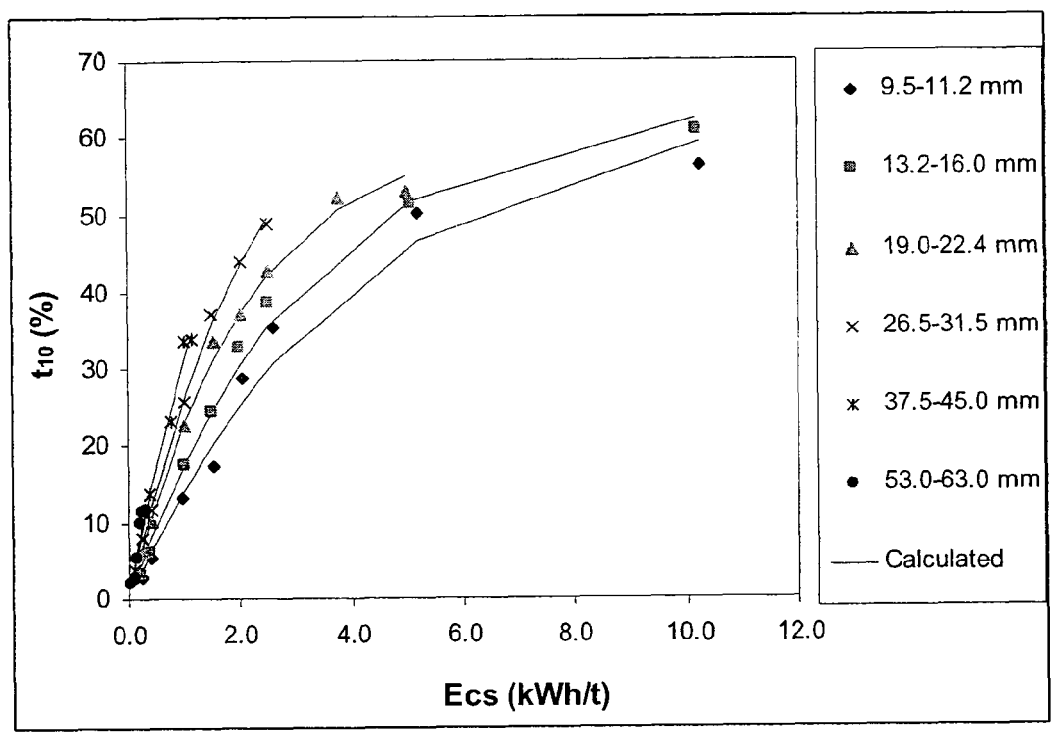
FIG. 6 is a graph showing the JK prior art breakage model fitted separately to each particle size using the A and b parameters calculated in FIG. 5 to produce a separate curve for each particle size.
Figure 7:
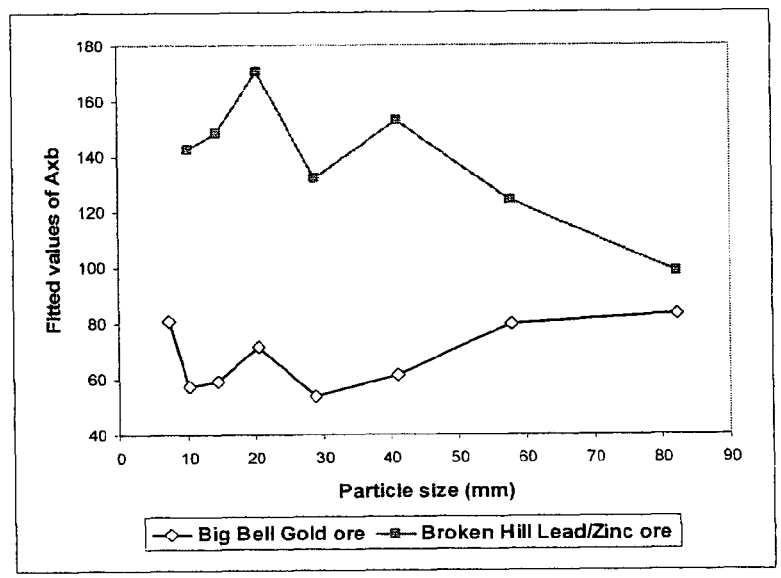
FIG. 7 is a graph plotting parameters A*b against particle size for two different materials.

In view of the loose fit of the parameters A and b with the data Applicant then experimented with some other options. One such option involved calculating the parameters A and b separately for each particle size using the same breakage test data shown in FIG. 3 above. FIG. 5 provides a table showing the separate calculations of parameters A and b for each of the different particle sizes. A family of curves was then plotted using the A and b values of FIG. 5 with each curve representing a different particle size and this is shown in FIG. 6. Again the test data is also plotted on the graph as points. It is immediately apparent that each of these curves fits the experimental data for that particle size better than the single curve in FIG. 4.

The Applicant then modeled the breakage of the same set of Mt Coot-tha particles using the new model defined in this invention. These results could then be compared directly against the prior art JK model results in FIG. 4.

The model according to the invention may be represented by the equation below:

$$t_{10} = M\{1 - \exp[-f_{mat} \cdot x \cdot k(E_{cs} - E_{min})]\} \tag{2'}$$

Firstly, Applicant used the breakage data shown in FIG. 3 to calculate the parameters M, $f_{mat}$ and D ($=x \cdot E_{min}$) for the new Equation 2' using curve fitting techniques. The Applicant calculated separate values of $f_{mat}$ for each particle size to take into account the effect of size on particle breakage. The values calculated for $f_{mat}$ were in fact different for the different particle sizes. One value for M was calculated for all the particle sizes as this parameter was not expected to vary with particle size.

The curve fitting techniques used an iterative calculation to calculate the values of the parameters M, D ($=x \cdot E_{min}$) and $f_{mat}$. These calculations are similar to those used to fit A and b to the prior art JK model and will therefore not be described further.

FIG. 8 shows the table of test data and the calculations that were carried out to fit M, D ($=x \cdot E_{min}$) and $f_{mat}$ to the test results. The values obtained for $f_{mat}$, D ($=x \cdot E_{min}$) and M are shown in FIG. 8. For the purpose of calculating the model parameters k was taken to be 1.

Figure 9:
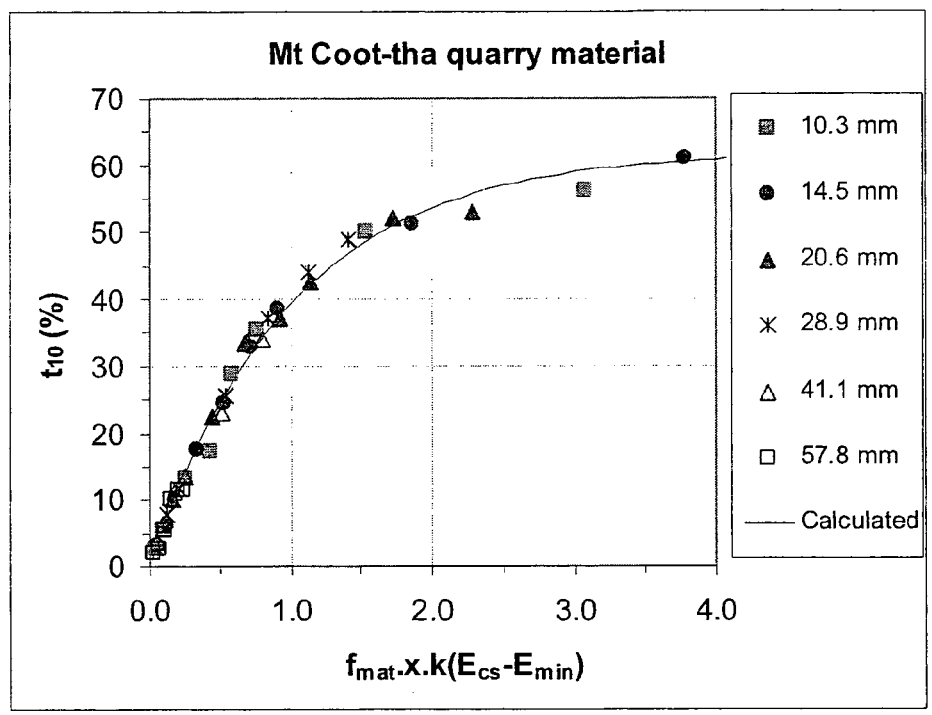
FIG. 9 is a graph showing the model of particle breakage according to this invention using the values for M and $f_{mat}$ fitted in FIG. 8.

FIG. 9 is a graph of $t_{10}$ (%) against $f_{mat} \cdot x \cdot k(E_{cs} - E_{min})$ which was plotted to show how closely the model fitted the test data.

The graph clearly shows that the model fits the test data well. The data points of all particle sizes are basically located on the trend line calculated by the model. This model therefore comprises a single equation that takes into effect the influence of particle size on particle breakage.

While this model described in the Equation 2 above provides a working model for particle breakage it does require $f_{mat}$ to be calculated separately for the different particle sizes.

Applicant therefore sought to find a way that the effect of particle size on $f_{mat}$ could be incorporated in the model equation. If this could be achieved then only a single set of parameters would need to be calculated for the model across all particle sizes.

Figure 10:
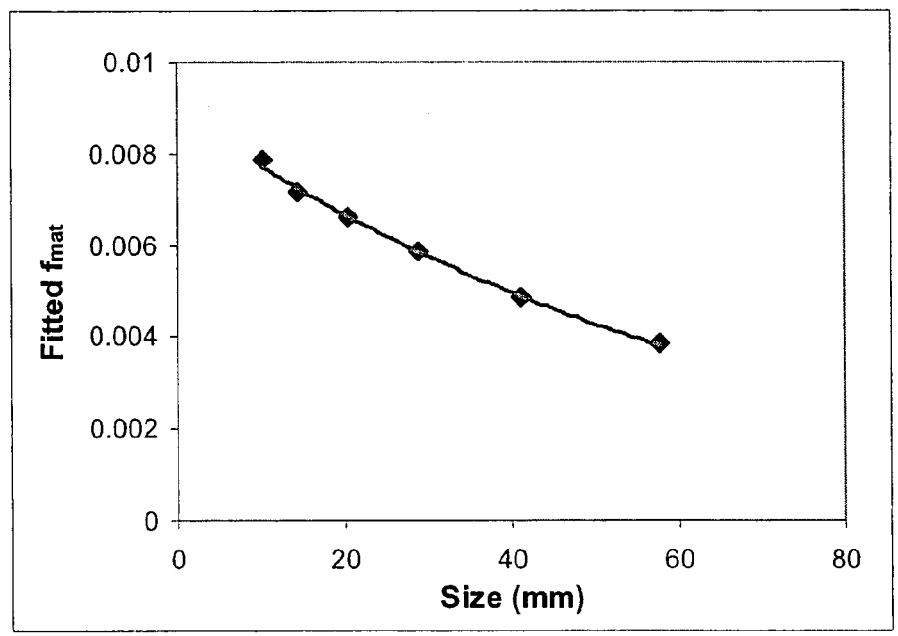
FIG. 10 is a graph of $f_{mat}$ fitted in FIG. 8 against the size of initial feed particles of that material.

Specifically, Applicant plotted fitted $f_{mat}$ against particle size for the Mt Coot-tha test data of FIGS. 3 and 8 using the $f_{mat}$ values fitted by the calculations shown in FIG. 8. The graph of $f_{mat}$ against particle size is shown in FIG. 10. The graph shows a smooth curve with a reasonable fit of the curve to the fitted $f_{mat}$ values. It is clear from this graph that the Applicant has identified that a consistent relation exists between $f_{mat}$ calculated from the curve fitting calculations and particle size. The Applicant has found the similar trends between the fitted $f_{mat}$ and particle size in many impact test data sets.

In addition Applicant has defined a mathematical model of the curve of $f_{mat}$ against particle size x, which is represented by the following power equation:

$$f_{mat} = p \times x^{-q} \qquad (4)$$

p and q are two constants defining the material properties and particle size effect on impact breakage.

Applicant has established that the relationship between $f_{mat}$ and particle size is so well represented by the power equation above that only three spaced points are required to fit the data to the curve and calculate p and q. This in itself is significant as it simplifies the calculation of the model parameters for the model as will be described in more detail below.

Applicant has also verified that the shape of the curve is the same for all materials. The only thing that varies is the decay rate of the curve and the position of the curve relative to the x and y axes.

Applicant then inserted this equation into the new model of the invention defined in Equation 2 above to produce the following equation (hereinafter called the modified form of the model of the invention).

$$t_{10} = M\{1 - \exp[-p \cdot x^{(1-q)} \cdot k(E_{cs} - E_{min})]\} \qquad (6)$$

This equation substitutes the power equation above for $f_{mat}$ and thus the parameters p and q replace $f_{mat}$.

The three parameters of this equation namely M, p, and q can be calculated in the same way as the other parameters described above with reference to FIGS. 3 and 8 by curve fitting techniques. This is done by fitting the particle breakage model to the test data and finding the best fit using the same statistical curve fitting techniques described above. In summary p and q are calculated using the curve fitting techniques instead of $f_{mat}$. When fitting the parameters the number of impact k is set at 1 and the energy threshold $E_{min}$ may also be set at zero if $E_{cs}$ is much larger than $E_{min}$.

If $t_{10}$ was plotted against $p \cdot x^{(1-q)} \cdot k(E_{cs} - E_{min})$ using the parameters p, q and M fitted above then a single trend line like that shown in FIG. 9 would be obtained.

A key breakthrough is that the power equation takes into account the effect of particle size and thus only one value of p and q needs to be calculated for all particle sizes. Thus once parameters p, q and M are fitted to the experimental data the single equation with one set of parameters can be used to define particle breakage across all particle sizes. This represents a big step forward over the prior art JK model. Not only does it factor in the effect of particle size very accurately, but it does this with one equation and a single set of parameters.

Advantageously, the method can be used to eliminate the need for high energy breakage tests. As illustrated in FIG. 9, all particle sizes (x) and all energies (Ecs) data fall on the same trend line. This indicates that low energy impact test data may be used to fit the new model parameters M, p, q and D, and the model parameters may be used to predict the high energy test results. There are many benefits in eliminating high energy impact testing, including for example reducing machine fabrication cost, decreasing noise level, reducing dust generation, and so on.

FIG. 12 shows how the test results for the Mt Coot-tha particulate material is reduced to obtain values for the parameters p, q, M and D ($= x \cdot E_{min}$) using curve fitting techniques. Once the parameters have been calculated then the modified model of the invention can be used to determine the breakage characteristics for a given size of particle of that material.

Applicant has also established that the relationship between $f_{mat}$ and particle size shown in FIG. 10 is so well represented by Equation 4 that fewer test results of particle breakage are required to determine the parameters for the modified model of the invention represented in Equation 6.

If the modified model of the invention was used to plot $t_{10}$ (%) against the specific input energy the single equation would produce a family of curves similar to those in shown in FIG. 6 from a single set of parameters for all particle sizes. Further the fit of the model to the data could be accomplished with substantially fewer test points.

Applicant has done a number of tests and has established that data for three different particle sizes at different energy levels giving a total of 7 test results can be used to accurately fit the three model parameters M, p and q to the model.

Specifically, FIG. 12 shows a table of the Mt Coot-tha test results for three particle sizes at various energy levels producing a total of seven test results. Values for M, D ($= x \cdot E_{min}$), p and q were calculated from these limited points using curve fitting methods and as shown these values are statistically similar to those calculated in FIG. 11.

The advantage of requiring only three particle sizes to be tested under the new invention instead of five particle sizes is that the cost of doing the test work is considerably less. Thus in addition to producing better results with the new model the number of tests required to determine the parameters for the model is less and the cost is therefore less.

The three particle sizes that are chosen should be spread across a size range with represent the size range of interest, for example sizes that are representative of feed material that is fed into a mill and which will be used in the simulation or modeling process later on. One particle size should be towards the fine end, one towards the middle of the size range and one towards the coarse end of the size range. In one example used by the Applicant the coarse size fraction chosen was about 37.5 mm, the middle size was about 20 mm, and the fine size was about 10 mm.

The Applicant has also identified equations that can be used to convert values of parameters M, p and q into A and b values for the old prior art JK model.

These equations are set out below:

$$A = M$$

$$b = 3600 \cdot p \cdot x^{(1-q)} \qquad 7)$$

where x is average particle size of interest. Therefore Equation 7 can be used to obtain A and b parameters for each particle size tested, or the average size used in the drop weight test for a particular material.

These equations can be used to obtain A and b parameters for any new particle breakage tests that are conducted. These new A and b values can be used to compare newly tested materials with materials for which A and b was determined under the old prior art JK model.

This is convenient because breakage characteristics of particles are often discussed and compared in terms of their A*b values.

Applicant conducted one further experiment to compare the prior art JK model with the model of the new invention.

The Mt Coot-tha tests in FIG. 3 were applied to the prior art model and forty two test results were used to calculate values for A and b. This produced a value for A of 59.07 and a value for b of 0.435 and a product of A and b of 25.70.

The results for M, p and q for the modified form of the new invention obtained with just seven test results as described above was used to calculate the $t_{10}$ values for the given energy levels and particle sizes given in FIG. 3. The calculated values of $t_{10}$ and their associated $E_{cs}$ values were used to fit A and b values for all particle sizes.

This produced a result for A of 56.81, a result for b of 0.475 and a product of A and b of 26.98. These results are very close to the results obtained for the prior art JK model even though they were obtained with vastly fewer test results. This result is illustrated in FIG. 13.

The comparative experimental work described above clearly demonstrates the accuracy and usefulness of the model of the invention. It also clearly demonstrates the working advantages that it confers over the prior art JK model.

The model of the invention has been validated by testing several types of ore with widely varying values of ore hardness. These ores had a hardness measured by A*b varying from 16 to 171, a particle size varying from 4.75 mm to 90 mm and a specific energy varying from 0.02 kW/h to 11 kWh/t. The model was validated by comparing the trend line against the test data and also by comparing the sum of the squared errors.

It is noted that Equation 7 may be used to calculate the A×b value for individual particle size or the averaged particle size. As large particles and small particles may exert different influences on the fitted A and b parameters, the applicant has further developed a more accurate method. The first step of the more accurate method includes using the new model (Equations 2, 3' and 4) to fit test data that may be collected at conditions different from the standard Drop Weight Tests (e.g. at reduced particle size and/or reduced energy levels). The second step includes using the parameters to predict for the standard Drop Weight Test (DWT) conditions (as if the DWT was conducted). The last step includes fitting Equation 1 to the predicted standard DWT data to generate the A and b values. This method has been validated and proved to be more accurate.

Applicant is confident that the model can be applied to a majority of ore particles that mining companies typically deal with. This includes coal and all the major metal ores such as gold, copper, lead/zinc and platinum.

Yet further the new model of the invention has also been tested against data on incremental breakage that has been published in the literature. The trend line produced by the model fitted the incremental breakage data closely.

Example of Usage and Implementation of the Invention

A mining company may wish to investigate the behavior and characteristics of a certain ore material being passed through a mill which may be an AG or SAG mill. To do this it needs to understand and characterize the breakage characteristics of the particles it is using. It also needs to obtain a measure of the fineness of the produce particles produced as a result of an impact of a certain amount of energy.

The first step in the process of modeling how a new material would break when subjected to impacts in a mill would be to do test work to obtain test data on the breakage of the particles using test equipment designed for this purpose. These apparatuses include a drop weight tester, a pendulum tester and any other apparatus for determining the size distribution of broken particles resulting from a certain impact energy.

Prior to conducting the actual tests the sample of material is pre-classified into different size fractions of different sizes. Three different size fractions are chosen and these are then tested in the drop weight apparatus in the usual way.

One of the size fractions of particles that is tested will be towards the coarse end, another size fraction will be towards the middle, and the last fraction will be towards the fine end. Each of these size fractions is tested at two or three different energy levels. The tests will produce a $t_{10}$ size distribution of the broken particles for each particle size that is tested and also at each energy level. This results in a table similar to that shown in FIG. 12 being produced.

The levels of energy that are selected for the particle breakage tests will usually depend on the comminution process that is being studied and/or modeled. For example where crushing and grinding operations are being studied then the selected energy level will be much greater than minimum energy threshold needed to break the particle. In crushing and grinding operations where large energy impacts occur then the levels of $E_{cs}$ would dominate $E_{min}$. As a result $E_{min}$ can be set at zero or a small constant. That is, the material constant D would be set to zero or a small constant, where $E_{min}=D/x$.

By contrast where particle breakage in a mill is being studied and there are low energy impacts and some incremental impacts then lower energy levels would be selected. In mills where lower energy impacts occur then $E_{min}$ is closer to $E_{cs}$ and $E_{min}$ should preferably to be taken into account.

$E_{min}$ can be determined by doing separate experiments with other impact test devices. These include the Hopkinson pressure bar and the Short Impact Load Cell (SILC). Alternatively $E_{min}$ could be calculated by curve fitting techniques.

These drop weight tests results are then reduced using the modified new model of the invention in Equation 6 above to produce fitted values for M, p, q and D.

The curve fitting may be conveniently performed using any mathematical data fitting program. Applicant uses the Solver function in Microsoft Excel but any other data fitting program could also be used.

This then produces a model with calculated parameters for the material that has been tested. As described above the model is used to predict the size distribution of the progeny particles produced by the collision. The results are expressed as the $t_{10}$ product fineness index.

For example the model could be used to predict how a material might break in a mill when subjected to an impact of a certain energy which is a typical energy of a collision that a particle might undergo in a mill. Further the model can be used to model the effect of incremental collisions of lesser energy that typically occur in a mill. The model does this by allowing for a plurality of collisions of certain energy. The number of collisions is represented in the model by the variable k.

The model can also be adapted to accommodate a plurality of collisions where the collisions have different energy. It does this by representing the equation as a summation of individual collisions. Effectively the applied specific energy of the different collisions is added together to produce an end result $t_{10}$.

After the parameters have been determined using the modified model of the invention in Equation 6 they will typically be stored in a database of such information for future use. The parameters that have been calculated can be used at a future date as long as the material has not changed and the drop weight test results that were originally obtained are still valid for the material being used at the later date.

In the prior art the breakage properties of materials have been characterized as the product of the A and b parameters, for example as A*b. A*b provides a number that gives some insight into the breakage properties of a certain material. It is often used by workers in the field to compare two or more materials.

Thus Applicant recognizes that it would be useful if the parameters ascertained for the model in Equation 6 could also be expressed in terms of the parameters A and b of the prior art Equation 1.

Applicant has developed some conversion equations that enable the M, p and q parameters of the Equation 6 of this invention to be converted into values for A and b and also A*b. The conversion equations developed by the Applicant are as follows:

$$A = M$$

$$b = 3600 \cdot p \cdot x^{(1-q)} \quad (7)$$

Thus whenever the parameters M, p and q for Equation 6 are calculated for a certain material these parameters can also be converted to A and b and also A*b values and stored in a database of A and b values alongside parameters A and b determined under the prior art JK model set out in Equation 1. The new A and b values obtained by converting M, p and q values to A and b using the conversion equations above can be compared with the A and b values determined previously using the prior art JK model.

Advantages

An advantage of the method of determining particle breakage characteristics described above is that the effect of particle size on breakage is explicitly incorporated into the model that is used. The model uses a number of parameters and once these parameters are calculated then the influence or effect of particle size on particle breakage is incorporated into the model. The parameter $f_{mat}$ while primarily a function of the material also incorporates the particle size effect into the model.

By factoring in the influence of particle size on breakage distribution the method of this invention produces better results than the prior art method discussed above that uses a set of parameters that are calculated for an average size of particle.

Consequently the model developed by this invention more accurately reflects what is going on in a mill and in turn this leads to better modeling results.

A further advantage of the new model described above is that the Applicant has discovered that there is a clear and consistent relationship between fitted $f_{mat}$ and particle size. Further Applicant has been able to describe this relationship mathematically by means of a power decay curve that is described above.

The $f_{mat}$ values are different for different materials and the decay rate of the power function is different for the different materials but the trend curve is the same for all materials and can be expressed in the form of the mathematical curve described above. Applicant has established that the equation that describes $f_{mat}$ as a function of particle size is sufficiently consistent that results only need to be inserted for three different particle sizes to fit the curve sufficiently accurately using statistical curve fitting techniques. This is a direct result of the closeness of the equation describing $f_{mat}$ as a function of particle size.

Flowing from the advantage immediately above is the further advantage that the method described above enables the breakage characteristics of a certain type of rock to be determined on the basis of fewer discrete particle breakage tests. It has the effect that fewer points are required to determine the parameters p and q.

Specifically Applicant believes that tests only need to be conducted on three different feed particle sizes at three different energy levels for the parameters p, q, and M to be calculated using standard curve fitting techniques. With the prior art JK model five different sizes of particles were tested at three different energy levels each giving a total of 15 tests. The tests are very time consuming particularly when the traditional drop weight or pendulum tests of individual particles are tested. Consequently they are expensive to perform.

The reduction in the number of tests required to be conducted will result in a reduction of the cost of doing the tests and of determining a set of parameters for the model for a particular material. This in turn could lead to more materials being tested and the materials being tested more frequently which in turn should lead to more accurate parameters being used to model a given material.

A further advantage of the method described above is that it can be used to determine the particle breakage behavior of particles that are larger than those that have been physically tested for particle breakage. For example the particle breakage testing apparatus may have size constraints on the size of particles that they can test. For example the maximum size of particles that can be tested in the breakage apparatus may be 25 mm. Alternatively the largest size of particle that can be provided by the mining companies for breakage testing may be 25 mm. The relationship between $f_{mat}$ and particle size described above can be used to ascertain the breakage characteristics of fractions that are coarser than say 25 mm.

Similarly there may be limits on the minimum size of particles that can be tested, e.g. in a drop weight test. The relationship between $f_{mat}$ and particle size described above can also be used to determine breakage properties of particles smaller than say 10 mm, e.g. about 5 mm.

A yet further advantage of the method described above is that the ore specific relationship between $t_{10}$, energy and particle size that is established by the method is common to all comminution processes that employ impact breakage. Thus the method provides a breakage function that can be applied to all unit operations involving particle breakage, including ball and hammer mill operations, AG and SAG mill operations and crusher and grinder operations. Specifically it can be used to simulate the comminution processes occurring in all these apparatuses, e.g. in the simulation software.

A yet further advantage of the method described above is that the ore specific parameters determined for the model of this invention can be converted into the A and b parameters that have traditionally been used to characterize or rank ore hardness. Typically the ore specific parameters were expressed by A and b values and also by the product A*b.

The parameters of the new model can be translated to the traditional A*b values using a set of equations that have been described above. Thus when test work is done and the parameters M, p and q is determined according to this invention these can be converted into a set of A and b values and also A*b values. This information can then be stored in databases alongside the traditionally obtained A and b values.

Applicant believes that mining companies will be more comfortable if the method can also be used to produce the traditional A and b parameters as this information can then be stored together with the previously obtained results which are of course expressed in terms of A and b values.

Another advantage of the method of determining the breakage distribution of particles according to this invention is that existing drop weight test data obtained from tests carried out previously and say stored in one of the databases discussed above can be used to determine the parameters for the new model. Thus the drop weight test results obtained using the prior art models can be reprocessed using the model of the current invention to produce parameters for the new model specific to that ore and that material. Thus where the material being processed through a mill is basically the same as that tested previously using the drop weight test (i.e. to produce parameters for the prior art JK model) these test results can be used to produce parameters for the new model. This is advantageous because the particle breakage tests do not need to be repeated. The point has been made above that these tests are time consuming and expensive.

Drop weight tests that have been conducted previously for the prior art JK model typically produced results for 5 different particle sizes across three different energy levels. The $t_{10}$ product fineness index was determined for each of these tests. This test data was used to calculate A and b using the traditional particle breakage model. This test data can be used to calculate the parameters p, q and M for the method of determining breakage according to this invention.

Mining companies have collected huge banks of ore breakage characterization data of the rock and ore bodies they are working with over many years. These test results can be used to produce parameters for the model of this invention without the need to conduct further particle tests. Specifically this data can now be processed according the method of this invention to produce p, q and M parameters for each of these ores.

It will of course be realised that the above has been given only by way of illustrative example of the invention and that all such modifications and variations thereto as would be apparent to persons skilled in the art are deemed to fall within the broad scope and ambit of the invention as herein set forth.

The invention claimed is:

1. A method of comminution of a particulate material including:
   predicting breakage properties of the particulate material when subjected to impact by calculating a breakage index for the particulate material using a following equation:

Breakage Index=$M\{1-\exp[-f_{mat} \cdot x \cdot k \cdot E]\}$ where:
   M represents a maximum breakage of particles for the particulate material;
   $f_{mat}$ is a material parameter that is a function of the particulate material being broken and particle size;
   x is an initial particle size of the particulate material prior to impact;
   E is a measure of specific energy applied to the particulate material;
   k is a number of impacts with specific energy E; and
   subjecting the particulate material to impact.

2. A method according to claim 1, wherein the measure of specific energy (E) that is applied to a particle is calculated by an equation:

$E=E_{cs}-E_{min}$ where:
   $E_{cs}$ is a mass specific breakage energy expressed in J/kg or kWh/t; and
   $E_{min}$ is a threshold energy below which breakage does not occur for particle size x expressed in J/kg or kWh/t.

3. A method according to claim 2, wherein M is expressed as a percentage and x is measured in units of m.

4. A method according to claim 3, wherein the material property $f_{mat}$ is measured in units of kg/J.m and $E_{cs}$ and $E_{min}$ are expressed in units of J/kg.

5. A method according to claim 4, wherein the threshold energy is calculated by an equation:

$E_{min}=D/x$ where:
   D is a material specific constant expressed in units of J/kg.m or kWh/t.m; and
   x is an average particle size in units of m.

6. A method according to claim 1, wherein the breakage index comprises a measure of a weight of broken particles below a certain size expressed as an amount relative to the weight of broken particles.

7. A method according to claim 6, wherein the breakage index is the weight of broken particles expressed as a percentage of the weight of the original feed particles that pass through a screen of a certain size.

8. A method according to claim 7, wherein the breakage index is the weight percentage of the broken particles passing through a screen having openings that are $1/10^{th}$ of a mean size of the feed particles.

9. A method according to claim 1, including converting the breakage index into a particle size distribution.

10. A method according to claim 9, wherein the particle size distribution is a cumulative particle size distribution.

11. A method according to claim 1, including determining values for the parameters M and $f_{mat}$ for the material that is being modeled.

12. A method according to claim 11, wherein the values for the parameters M and $f_{mat}$ are determined by obtaining test results on the breakage of particles of particular sizes and then calculating values for M and $f_{mat}$ using statistical curve fitting techniques.

13. A method according to claim 1, wherein the material breakage parameter ($f_{mat}$) for a material is determined as a function of the size of a particle, the method including:
    calculating the material breakage parameter according to a following equation:

material breakage parameter $f_{mat.}=p \times x^{-q}$ where:
    x is the initial particle size prior to breakage; and
    p and q are material parameters that take into account an effect that particle size has on impact breakage.

14. A method according to claim 13, including determining values for parameters p and q by fitting test data to the material breakage parameter equation.

15. A method of communition of a particulate material including:
    predicting breakage properties of the particulate material when subjected to impact by calculating a $t_{10}$ breakage index for the particulate material using a following equation:

$t_{10}=M\{1-\exp[-p \times x^{(1-q)} \cdot k(E_{cs}-E_{min})]\}$ where:
    M represents a maximum breakage of particles for the particulate material;
    $E_{cs}$ is a mass specific breakage energy of the impact;
    $E_{min}$ is a threshold energy below which breakage does not occur;
    k is a number of impacts with specific energy ($E_{cs}-E_{min}$);
    x is a initial particle size prior to impact;
    p and q are material parameters that take into account an effect that particle size has on impact breakage; and
    subjecting the particulate material to impact.

* * * * *